(12) United States Patent
Logue et al.

(10) Patent No.: US 6,946,833 B1
(45) Date of Patent: Sep. 20, 2005

(54) POLAR COORDINATES SENSOR HAVING AN IMPROVED FLUX SUSPENSION SYSTEM AND EXCITATION METHOD

(76) Inventors: Delmar Leon Logue, R.R. #1, Box 70, Herrick, IL (US) 62431; Stephen John Logue, 602 E. Cleveland St., Taylorville, IL (US) 62568

( * ) Notice: Subject to any disclaimer, the term of this patent is extended or adjusted under 35 U.S.C. 154(b) by 0 days.

(21) Appl. No.: 10/349,526

(22) Filed: Jan. 22, 2003

Related U.S. Application Data

(63) Continuation-in-part of application No. 09/873,838, filed on Jun. 4, 2001, now Pat. No. 6,580,267.

(51) Int. Cl.$^7$ ........................ G01N 27/72; G01R 33/12
(52) U.S. Cl. ........................ 324/240; 324/242; 324/225
(58) Field of Search .............................. 324/240, 225, 324/232, 241, 243, 238, 239, 207.17, 207.18, 324/207.19, 228, 233, 234, 242, 262

(56) References Cited

U.S. PATENT DOCUMENTS

| | | | |
|---|---|---|---|
| 5,172,055 A * | 12/1992 | Horn | 324/207.16 |
| 5,404,101 A * | 4/1995 | Logue | 324/207.17 |
| 5,548,212 A * | 8/1996 | Logue | 324/229 |
| 5,793,204 A * | 8/1998 | Logue | 324/228 |
| 5,909,118 A * | 6/1999 | Logue | 324/240 |
| 5,939,880 A * | 8/1999 | Logue | 324/232 |
| 6,265,871 B1 * | 7/2001 | Logue et al. | 324/240 |
| 6,271,664 B1 * | 8/2001 | Logue | 324/240 |
| 6,580,267 B2 * | 6/2003 | Logue et al. | 324/240 |

* cited by examiner

Primary Examiner—Jay Patidar

(57) ABSTRACT

An improved polar coordinates sensor comprising a pot-core half having a concentric winding window surrounded by a washer-like high conductive Lenz lens. A toroidal core stack concentrically disposed at the base end of the pot-core half, the pot-core half, Lenz lens and the toroidal core stack being disposed coaxially with aligned winding windows. X-y coordinates excitation winding distributions being shuttled through the coaxial aligned windows to encircle the cross-section of pot-core half, Lenz lens and toroidal core stack forming a series circuit. X-y excitation currents being connected to the excitation distributions to induce a hemispherical driving field. The inductive reactance of the series coupled toroidal core stack allows an increased degree of differential redistribution of driving flux in response to probe tilt. A rotating/non-rotating excitation method, of which a source of the x-y signals may include electromechanical resolver type waveforms. The sensor is further expanded by adding an outer radii auxiliary driving assembly comprising a toroid core encased by a second Lenz lens series coupled to a larger diameter toroid inductive reactance, providing the capability of two independent rotating/non-rotation concentric interacting driving fields. Further disclosed is a polar coordinates sensor having an air-core pick-up coil. Further disclosed is a "hidden metal edge mapper" for aircraft construction utilizing a tilted polar sensor indicating target by signal phase angle.

10 Claims, 3 Drawing Sheets

POLAR COORDINATES SENSOR HAVING AN IMPROVED FLUX SUSPENSION SYSTEM AND EXCITATION METHOD

CROSS-REFERENCE TO RELATED APPLICATIONS

This Patent application is a continuation-in-part of patent application Ser. No. 09/873,838 filed Jun. 4, 2001 now U.S. Pat. No. 6,580,267.

BACKGROUND OF THE INVENTION

All eddy current induction/detection devices are obviously governed by Lenz's reflective law. A permanent magnet floating above a superconductor (Meissner effect) illustrates a literal flux suspension system. Reciprocally, the hemispherical driving flux fringing from the polar coordinates sensor in Logue U.S. Pat. No. 5,909,118 that allowed several degrees of probe tilt, was the result of a flux suspension system provided by an annular air gap between the driving core and the pick-up core. Copending Logue et al. patent application Ser. No. 09/873,838 disclosed an integral driving/sensing pot-core half wherein the flux suspension system comprised connecting the poly-phase excitation windings in a series ring; thus providing a greater degree of differential redistribution of the H field in response to probe tilt. The present disclosure adds a high premeability ballast toroidal inductance in series with the x-y coordinates excitation turns, in effect a differential flux equalization means.

Remember diameterwise excitation of a toroidal core (x-y axes of permeability) is not a closed loop, therefore, high frequency response is good.

The mechanical equivalent is left to right differential linkage means and a longer stabilizer spring travel in an automobile suspension system.

Early Logue eddy current devices were called "polar coordinates" sensors e.g. Logue U.S. Pat. No. 5,939,880 comprising a pick-up core (pot-core half) and a driving core (poly-phase motor stator) i.e. a concentric arrangment being magnetically neutralized due to inherent orthogonality between driving and sensing axes of permeability. Logue et. al. U.S. Pat. No. 6,265,871 taught eddy current induction-detection by utilization of a rotating diametric dipole sensing hemisphere/s (see FIG. 1) fringing from the equatorial plane of a toroidal core 55xx. The term "polar coordinates sensor" is intended to convey more than planar geometry, by prior description i.e. "a hemispherical sensing pattern" (Logue U.S. Pat. No. 5,548,212) fringing diameter-wise from the equatorial plane of a high permeability toroidal core/s. Therefore, "polar coordinates" also includes varying degrees of Lenz latitude of eddy current depth within the workpiece. Obviously the reciprocal of polar coordinates is x-y coordinates. To avoid ambiguity, "polar coordinates sensor" will continue be the generic term used herein.

FIELD OF THE INVENTION

The generic term "toroidal" includes various closed geometric shapes e.g. pot-core halves (even a plurality of concentric poles as in Logue U.S. Pat. No. 5,404,101), bell (flared trumpet) conical shapes i.e. a television deflection yoke. Firstly, the apparatus-means of the invention comprises a high permeability ballast toroid core series-wound with a driving-sensing pot-core half, the toroid acting as an inductive reactance ballast in a passive differential flux suspension system. Secondly, the pot-core half (pick-up element) is surrounded by a high conductive (e.g. copper/silver) Lenz lens for focusing the driving flux.

Thirdly the method-means of the invention comprises an unsymmetrical angular resolver type of driving excitation. In addition to this, a television/radar raster/scan type of x-y axes excitation method is described as first disclosed in copending Logue et al. application Ser. No. 09/873,838.

Excerpt from Logue application Ser. No. 09/873,838

"Other Excitation Methods"

"Just as a toroidal deflection yoke around the neck of a TV picture tube magnetically moves the electron beam/s to any location on the screen according to a predetermined program, so also the subject method moves the eddy current on (horizonal-vertical) x-y coordinates. As part of this disclosure, an eddy current scan pattern similar to a television raster may be generated in a planar workpiece by polar coordinates probe utilizing a programable (software) method. Radar type scans e.g. plan-position indicator (PPI) is also a programable method."

SUMMARY OF THE INVENTION

Increasing the degree of tiltability in the polar coordinates sensor is a primary object of the invention. This means the flaw signature is retained over a greater probe tilt angle.

A diameterwise magnetization of toroidal inductance is added in series with the x-y currents exciting the mentioned driving-sensing pot-core half.

A further utility of the embodiments of the invention is: a "hidden metal edge mapper" for use in aircraft splice-joint construction. In such aerospace industry, it is necessary to drill holes in a slice joint centering on hidden framework or a predetermined distance from a sub-layer edge from the blind side (see Horn U.S. Pat. No. 5,172,055 for more detail of this need). Further, coaxially aligning tool bits on opposite sides of a large thick aluminum panel, may be accomplished by x-y coordinates nulling a polar coordinates sensor over a cylindrical ferrous target from the blind side and utilizing a marking means upon each side.

Further, by tilting the z-axis of the polar sensor (probe/s of the invention) a few degrees toward/away from the direction of probe travel a reference azimuth-phase angle signal indicative of the hidden edge is generated, any deviation +−in phase angle may be utilized to control automatic steering of a propelling and seam marking means.

Alternative Conductive Materials

The disclosure additionally covers the use of conducting metals such as mu-metal 1020 steel, stainless steels, for forming the probe structure/s termed "Lenz-reflector", although the example probe signals displayed herein utilized copper to form the subject Lenz-reflector. All conducting materials are included. Even further, interleaved ferrous/non-ferrous laminate may be utilized for such driving field blocking/focusing geometry.

DETAILED DESCRIPTION OF THE INVENTION

Remember, all cross-sectional partial views of toroidal cores, Lenz-lens, grooves, air-gaps and toroidal-windings represent a complete revolution around the z-axis. Also remember, the fragmentary method of drawing a few turns of magnet wire (with/without connecting leads) linking a toroid, pot-core and/or Lenz-reflector represent entire/complete circumferential/toroidal x-y coordinates coverage.

The high permeability materials utilized in the invention include all soft magnetic materials including tape materials e.g. Magnesil*, Orthonol*, Permalloy*, Supermalloy*, Supermendur* and all amorphous magnetic materials: e.g. Metglas* made by Honeywell*. Even further, powdered iron and ferrites.

Basics

Figure 1:
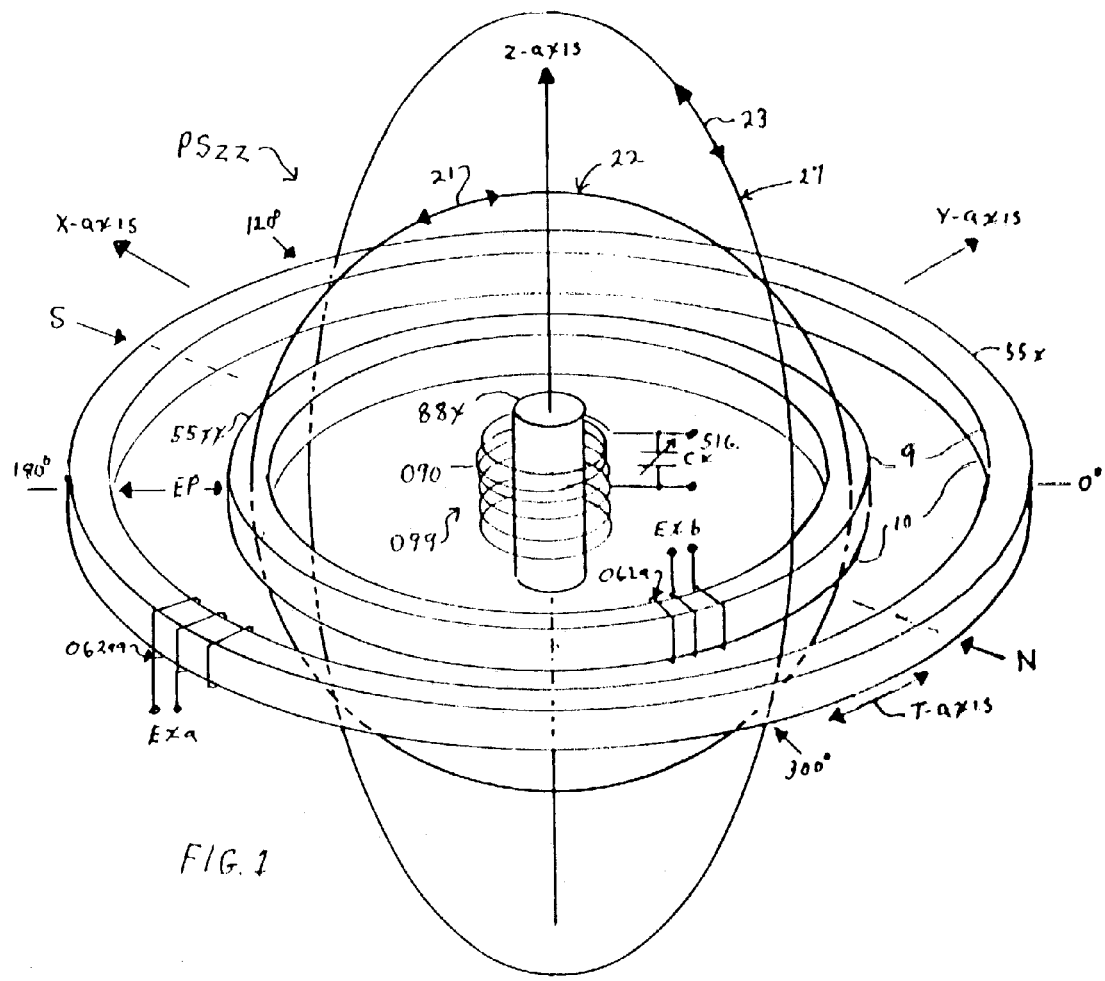
FIG. 1, is a perspective view of concentric toroid cores 55x,55xx illustrating two concentric azimuthal hemispheres of effective flux within the driving pattern of embodiment II of the disclosure.

Isotropic magnetically soft materials having toroidal geometry may allow several directions of effective magnetization simultaneously provided the vectorial flux density is below the saturation point. Thus a simple toroid has several "axes of permeability" as pictorially shown in FIG. 1: e.g. x-y-z axes, t-axis (toroidal). Let us first analyze the magnetization of outer radii toroid $55x$ excited on x-y coordinates by x-y coordinates excitation windings $062aa$ (drawn in fragmentary). Bihemispherical circle 23 represents the mean (effective) flux fringing from equatorial plane EP i.e. outer flux shell 27 of probe PSzz, this shell is formed by stepwise interposed active/silent azimuth headings (only the 30–120 diameter is shown) of hemispherical flux lines fringing from the equatorial plane EP of core $55x$. Disposed concentrically within flux shell 27 is inner flux shell 22 (only the 0–180 diameter is shown) fringing from the equatorial plane EP of toroid $55xx$, represented by hemisphere 21. X-y excitation winding distributions $062a$ (shown in partial) are uniformly wound around $55xx$, and connected to a x-y generator (not shown) via leads Exb. Notice, excitation windings $062aa$, $062a$, are electrically isolated, thus may be individually connected to separate x-y (or poly-phase) excitation generators providing a number of independent or interlocking angular phase eddy current patterns e.g. stepwise/continuous, plus various frequency/amplitude modulation modes e.g. elliptical (Logue U.S. Pat. No. 5,793,204).

For correspondency with the orthogonal driving/detection elements of the disclosed embodiments, an asymmetric flux pick-up assembly 099 comprising, a high permeability rod core $88x$ wound with a pick-up coil 090 having signal leads SIG. and shunted by variable capacitor Cx, all pick-up elements are coaxial on the z-axis for a signal null.

Referring again to FIG. 1, when excitation currents flow through x-y (also includes poly-phase configurations) winding distributions $062aa$/$062a$ (shown in partial) from a current generator/s (not shown) connected to respective terminals Exa/Exb, a diameterwise dipole S N fringes from the equatorial plane EP of toroid/s $55x$/$55xx$, forming a hemispherical driving field/s 21/23. Depending on the excitation program field/s 21/23 may have zero angular velocity (x-y stepwise) or may advance e.g. 0–360 degrees unipolar (x-y or poly-phase) constant or ramping angular velocity. Said another way, this angular advancment may be linear, ramping, or stepwise burst/silent. The term "burst" refers to a number of x-y excitation alternations centered on a given azimuth. The term "silent" refers to a predetermined number of azimuth degrees of zero amplitude x-y excitation. Pick-up coil 8 generates a signal on terminals Ta in response to an asymmetry in the sensing pattern. Hb designates the complementary fringing hemisphere. Toroid/s $55x$,$55xx$ have top and bottom sensing planes 9, 10.

Method of Excitation

A non rotating (stepwise) excitation mode may be seen from the teaching of Logue U.S. Pat. No. 5,793,204 where the minor elliptical generation axis may be reduced to zero. This is where a plurality of ellipses are generated at one azimuth heading i.e. zero angular velocity. Therefore this disclosure emphasizes x-y coordinate windings and excitation. Alternately, poly-phase excitation (constant or ramping angular velocity) may be utilized to drive all disclosed devices.

Figure 2:
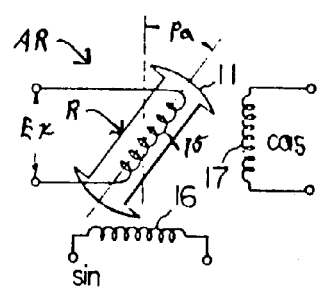
FIG. 2, is a vectorial diagram of a prior art inductive angular resolver vectorially illustrating an excitation generator/method.
Figure 3:
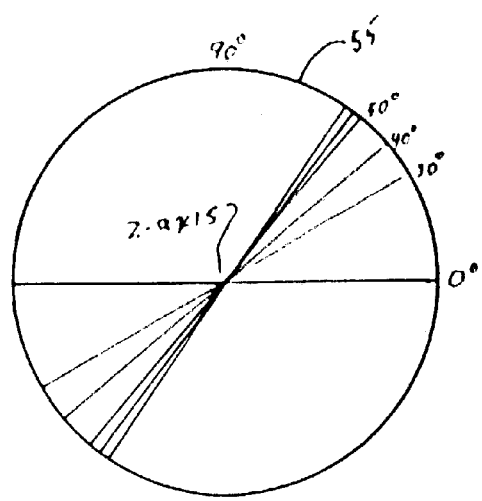
FIG. 3, is a polar diagram illustrating a programable stepwise active/silent eddy current induction method.

FIG. 2 is schematic of an angular resolver AR e.g. Clifton Precision Products Co. phase shifter unsymmetrical resolver type PS-17-E-1 having rotor R and orthogonal stator windings 16 (terminals SIN) and 17 (terminals COS). Excitation current from an external signal generator (not shown) is applied to coil 15 via terminals Ex magnetizing high permeability rotor core 11. Rotor R has two generic recoprocal induction modes i.e. angular velocity and flux level (both AC and DC are covered). Condition 1: Rotor R rotates at a constant angular velocity and has a constant flux level. Result: Sine-cosine signals SIN, COS, produce a single frequency rotating magnetic field of constant amplitude in a 2 phase polar coordinates sensor. Condition 2: Rotor R held stationary (static) at a given angular position and winding 15 excited at a given constant frequency. Result: A zero angular velocity (stationary) the driving dipole fringing diameterwise across the polar coordinates sensor sensing face i.e. the annular face of a pot-core half. Driving vectors are shown at 0 and 10 degrees in FIG. 3 i.e. the same as X-axis only excitation. Although, a mechanical resolver driven by a variable speed motor could actually be utilized as a signal generator, the disclosed stepwise exitation method (FIG. 3) is preferably generated by digital computer means as taught in Logue U.S. Pat. No. 5,793,204. Ramping the poly-phase excitation frequency generates a sub-frequency flaw-signal, having an oscillatory build-up on the z-axis (Logue U.S. Pat. No. 5,909,118), resulting in a rotational additive charge between the terminals of a "tank" capacitor connected across the pick-up coil leads.

To avoid ambiguity between description and appended claims we must explore the available terminology to designate a field focusing means (magnetic lens/es), from the terms: high-reluctance, electromagnetic-shield, skin-depth, Lenz's law, current loop, shading-coil, magnetic-lens, etc. Even more complex, an integral Tesla-transformer-driver arranged between outer radii Lenz-reflectors (second embodiment) interacting with a layered aluminum workpiece, becomes a "compound shaded pole" combination generating-detecting a degree of "second-secondary" effects.

The inherent-infinite imbalance-gain of the subject sensor exhibits traveling magnetic field and wave-guide effects as a perfect null is approached, meaning: exactness of excitation turns placement and sensing-face geometry (all elements) rivals waveguide construction (exhibits exacting geometric effects as though much higher frequencies were involved).

Inspite of common usage of the term high-reluctance as a "skin-depth" value, the eddy current phenomenon is a shorted-turn secondary of a transformer. Transformer secondary winding/s are never referred as a high reluctance (air-gap concatenation). The term "Lenz lens" conveys the desired focusing concept more adequately.

Embodimemt One

Figure 4:
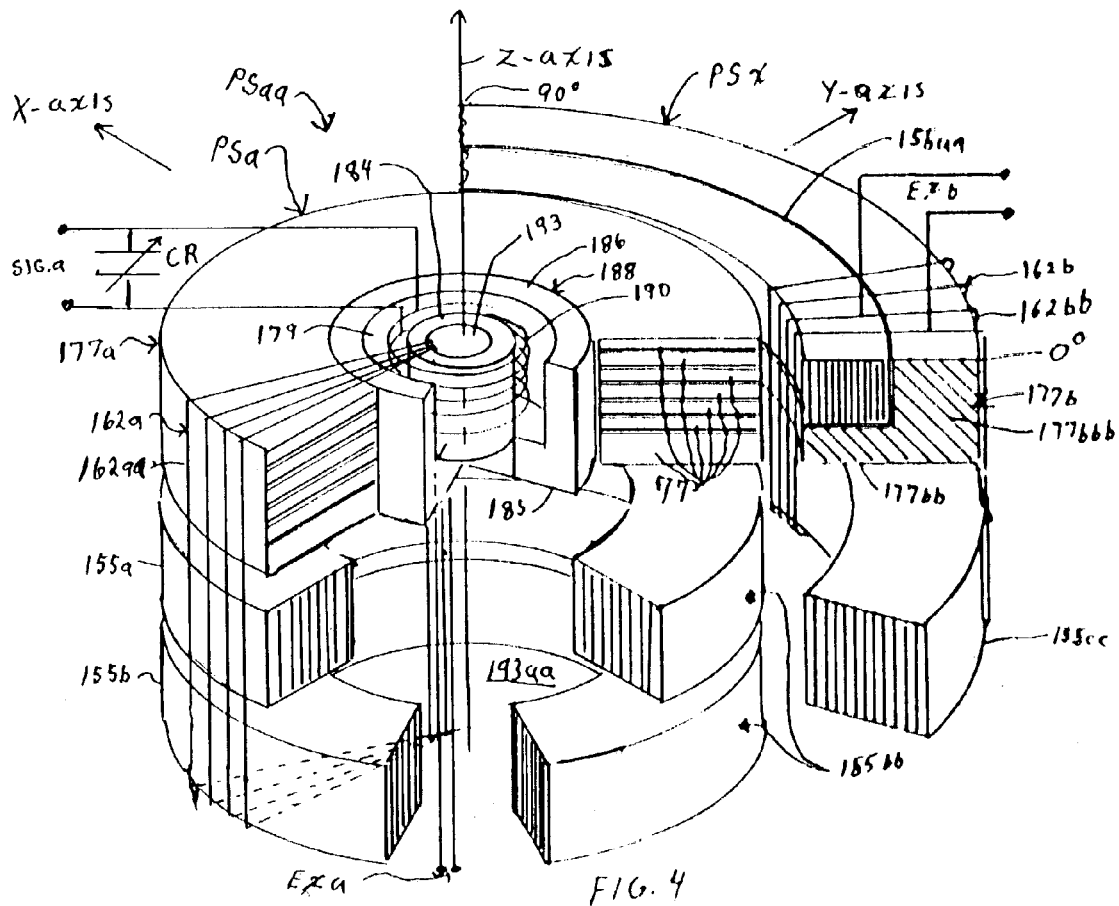
FIG. 4, is a sectional/perspective view of an improved polar coordinates sensor utilizing two sub-radii ballast toroids and a laminated Lenz lens, plus a greater-radii driving toroid series wound with a second ballast toroid and a greater-radii Lenz lens.

The generic polar coordinates sensor is designated PSaa in FIG. 4, has an optional outer radii elements as decribed under Variant II.

Variant I

We first describe polar coordinates sensor PSa (exclusive of auxiliary outer radii field means PSx shown between 0–90 degrees) in FIG. 4. PSa comprises a pot-core half 188, an improved Lenz reflector 177a, coaxially stacked with two high permeability ballast toroids 155a,155b, forming a coaxial winding window 193aa.

Pot-core half 188 (the pick-up core) is formed of a high permeability ferrite having an outer cylindrical pole 186 concentrically enclosing a central tubular pole 184 forming winding window 193. Poles 186,184, are connected at a first end by a base portion 185, leaving an annular pick-up coil space 179. A pick-up coil 190 having many turns is wound in space 179 shunted by variable capacitor. Our prototype utilized Magnetics* pot-core half OW42318.

The asymmetric (flaw) flux signal appears at terminals SIG.a. Pick-up core 188 is tightly fit with an improved Lenz reflector 177a formed of a nonferrous material such as copper/silver being in the form of a thick washer. The improvment being a laminate of several flat washers 77 glued rigidly together reducing longitudinal eddy current, yet retaining planar (focusing) eddy currents, thus probe battery efficiency is increased. Poly-phase/stepwise driving excitation is conveyed to X-Y-axes winding distributions 162a by leads Exa (windings and leads are shown in partial). The plane of individual winding turns 162aa should align with the Z-axis and leads Exa should be twisted and dressed near the Z-axes as shown to prevent stray coupling. Respectfully, X and Y axes coil pairs are connected diameterwise in series (all leads and connections are made near the Z-axis).

Our prototype utilized Allied Signal* Metglas* MP3210P-4AF cores to assemble inductance 155bb.

A non-metallic hollow coaxial alignment spool (not shown) may be fitted in toroidal stack window 193aa for correct assembly glueing, then a cylindrical plastic housing (also not shown) forms a hand grip (coaxial assembly being held together with a rigid potting compound).

Variant II

Now combining PSa with PSx (all elements shown in FIG. 4) we have variant designated PSaa, and referenced as "a variable-azimuthal-concentric-hemispherical" eddy current probe.

An outer radii auxiliary driving assembly PSx comprises an outer high permeability driving toroid 155aa encased within an outer cylindrical a high conductive (copper) auxiliary Lenz lens (reflector) 177a. The sectional cut shows 177a has an longitudinal rim 177aaa tightly fit concentric around the outer diameter of 155aa and a radial flange touching the backplane of 155aa. A larger diameter high permeability high cross-section ballast toroid 155cc is concentrically disposed adjacent the back of 177b. The cross-section of all three elements 155aa,177b 155cc, is encircled by poly-phase excitation winding distributions 162b (drawn in partial) connected by leads Exb to an auxiliary x-y-axes current amplifier driven by a programable computerized generator (not shown). Obviously all elements of eddy current probe PSaa are arranged concentrically around the Z-axis for a null signal at SIG.a. Eddy current probe PSaa may be excited by a variety of modes of current modulation:

1) Two x-y axes generators, each forming a zero angular velocity field. 2) Two x-y axes generators, individually forming a stepwise azimuthal incrementing field, including unidirectional and bidrectional active/silent azimuthal increments.

3) Two poly-phase generators, individually forming a rotating field. 4) Two electromechanical angular resolvers, individually generating x and y fields from the stator, with wound rotors individually excited by currents DC or modulated in e.g. frequency/amplitude.

Embodiment Two

Variant 1

Figure 6:
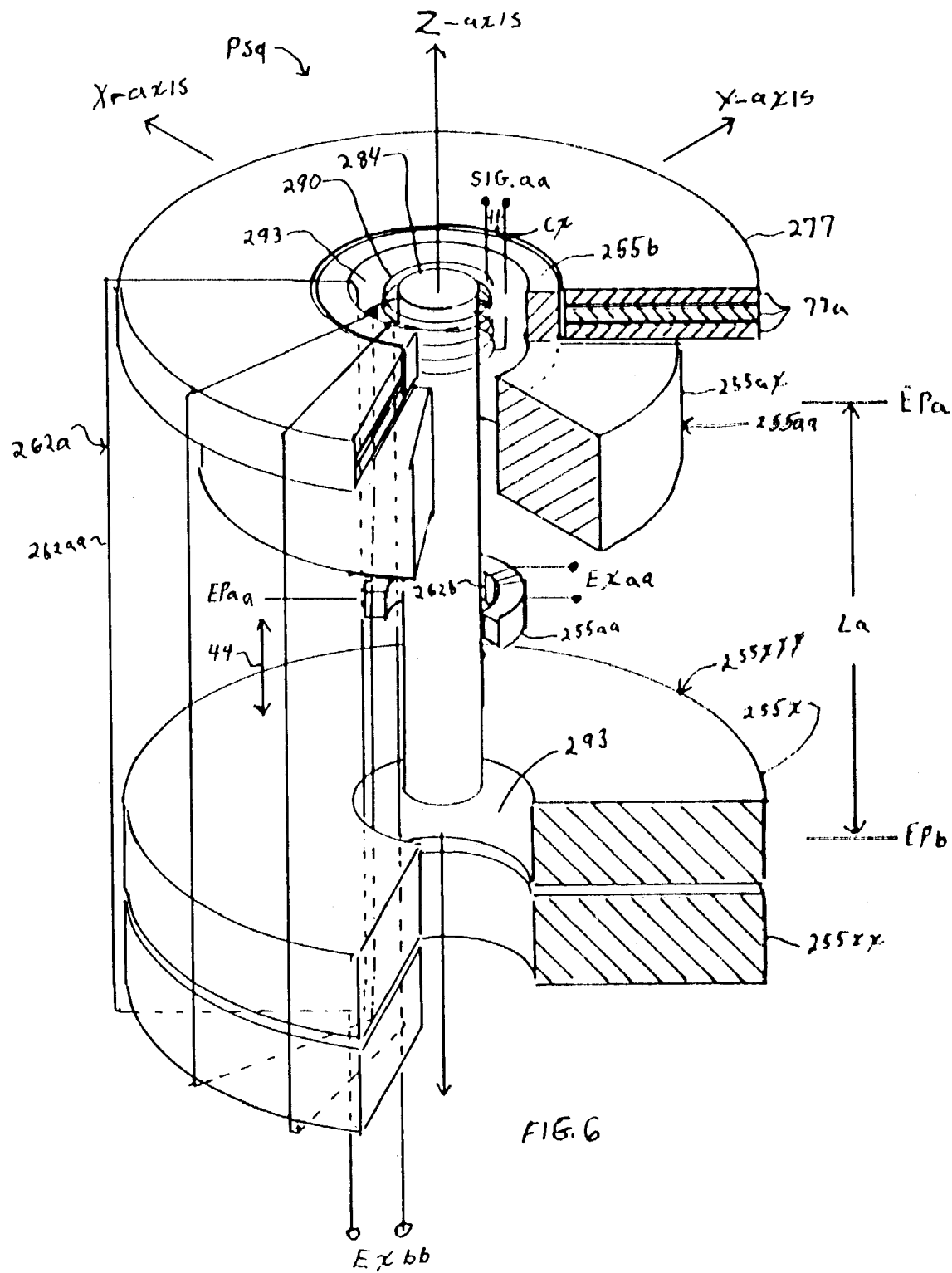
FIG. 6, is a section/perspective view of another embodiment of eddy current probe utilizing a toroidal ballast core assembly and toroid-rod driver-sensing sensing arrangement.

FIG. 6, is a sectional/perspective view of polar coordinates sensor PSq, some of the improvements are: 1) Combination driving toroid 255aa comprising: integrally formed longitudinal flange 255b and radial flange 255ax.

2) A large diameter laminated Lenz reflector 277, formed of a stack high conductive (e.g. copper) of flat washers 77a individually insulated and bonded together, the total thickness is such that a phase shifted potion of the hemispherical component (23 in FIG. 1) fringing from radial flange 255ax passing through 277 and into a workpiece is displaced substantially in phase depending on lens thickness and x-y excitation frequency.

The subject "improved flux suspension system" includes a pair of high permeability stacked toroids 255x,255xx, forming toroidal ballast 255xxx, having coaxially aligned winding windows 293. Toroidal ballast 255xxx, is coaxially aligned an adjustable displacement La, at the rear of toroidal driving core 255aa.

La represents the assembly adjustable distance between equatorial planes EPa,EPb, of cores 255ax,255xxx, respectively.

Coaxially disposed within the winding window 293 of toroidal core 255aax is a high permeability ferrite rod 284, disposed coaxially on the z-axis, having a pick-up coil 290 of many turns wound around a first end (sensing/top end) having signal out leads SIG.aa shunted by a series resonant capacitor Cx. The opposite/bottom portion of ferrite rod 284 is cocentrically surrounded by a high permeability flux gating toroid 255aa, toroidally wound with a saturating coil 262b having leads EXaa, connected to a programable current controller (not shown). The equatorial plane EPaa is adjusted (axial displacement 44) during assembly for an optimum flux gating of the complenentary hemispherial fringing from 255aa (see FIG. 1), and the asymmetric (flaw) flux return path to toroidal reactor core 255xxx.

The complementary hemisphere (not drawn) of 255aa is also the return path for any asymmetric Lenz reflection in the driving pattern (not shown). A toroidal flux gating principle is disclosed in Alldredge U.S. Pat. No. 2,856,581. Eddy current probe PSq has an improved flux suspension comprising ballast stack 255xxx, comprising a high permeability toroidal core pair 255x,255xx forming coaxial window 293.

Self Nulling

We now explain another intrinsic self nulling action of the subject flux suspension (limited to FIG. 6).

Figure 5:
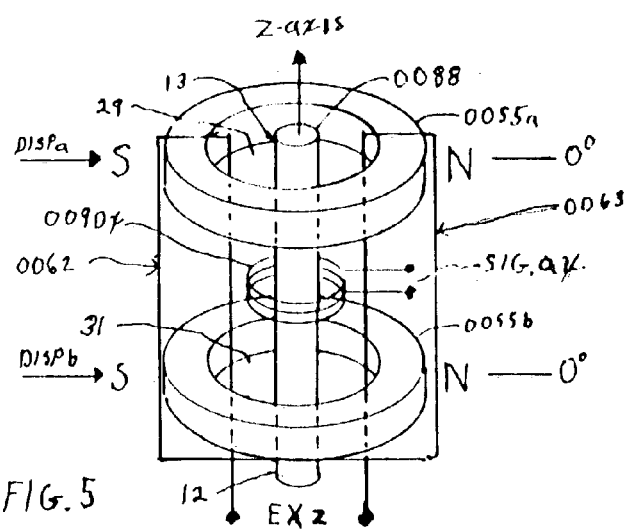
FIG. 5, is an isometric view a pair of high permeability toroids and z-axis ferrite pick-up core to geometrically illustrate how the subject flux suspension also makes possible self-nulling in response to probe tilt.

Lateral shifting of the flux density within stacked toroidal cores (255aa,255xxx, in FIG. 6) i.e. shifting of the driving flux centroid in which pick-up rod 284 is subsubmerged, will be the crux of this treatise. This is lateral movement of the z-axis resulting from probe tilt or rectangular (T V raster) excitation. FIG. 5 has two high permeability toroids 0055a, 0056b, coaxially anigned but seperated by a distance approximately equal to the diameter of 0055a/0055b. A high permeability ferrite rod 0088, having a sensing end 13 and a rear end 12, is coaxially disposed within the winding windows 29, 31 of toroids 0055a,0055b, with a pick-up coil 0090x, wound coaxially at approximately the center of rod 0088 length, having signal leads SIG.ax. FIG. 5 also illustrates the preferred x-y excitation winding method i.e. diameterwise series connected quadrant coils 0062,0063, to induce "like poles parallel" in response to current flowing via leads EXz. The illustrated magnetizations SN of 0055a, 0055b, are actually induced by a pair of parallel quadature coils not shown. As probe tilt or a rectangular driving flux is generated, the centroid of flux with toroids 0055a,0055b, both laterally shift e.g. to the right (arrows Dispa, Dispb). Inasmuch as toroids 0055a,0055b, are linked by the same excitation coils 0062,0063, the resultant lateral displacement of ends 12,13, are approximately the same, the desired "flaw signal retention" is improved.

Assembly Advice

To prevent cutting of magnet wire insulation; all coil-touching surfaces of the Lenz-reflector should be coated with a thin insulating means (casing) before winding.

We claim:

1. A polar coordinates sensor generating a hemispherical flux
   in a conductive workpiece and for detecting an asymmetry in the said hemispherical flux and generating an asymmetric signal; said sensor having an improved flux suspension system comprising:
   a) a toroidal core formed of a high permeability material taking the shape of a slotless pot-core half, and;
   said pot-core half further comprising:
   a central cylindrical pole concentrically surrounded by a cylindrical outer pole, leaving an interposed annular pick-up coil space, and a base portion for connecting said central and outer poles at one end, a cylindrical winding window coaxially disposed in the central cylindrical pole extending the axial length of the pot-core half, the opposite end forming an annular sensing face, and;
   a pick-up coil of many turns wound around central cylindrical pole for generating an asymmetric flux signal;
   said pick-up coil shunted by a variable capacitor forming an oscillatory tank circuit;
   the axis of said pick-up coil being orthogonal to the said hemispherical flux for a signal null when the eddy current reflection is symmetrical, and;
   a high conductivity laminated Lenz lens taking the shape of a thick washer having a cylindrical bore coaxially disposed within and extending the longitudinal length of the said washer, the said laminated Lenz lens formed of a stack of thin flat washers formed of a high conductive material;
   the axial length of the said Lenz lens being at least the longitudinal length of the said pot-core half;
   the said Lenz lens being tightly fit concentrically around the pot-core half, for forming an integral field focusing aperture at a first cylindrical end, the said base portion being disposed at a second cylindrical end;
   the said flux suspension system further comprising,
   at least two high premeability toroid cores, having respective winding windows coaxially stacked to define a toroidal reactor;
   the said toroidal reactor being disposed at the said second cylindrical end in coaxial alignment with the pot-core winding window;
   x-y-axes excitation winding distributions having connecting leads, shuttled through the said winding windows, and further, all excitation turns encompassing the pick-up coil, the pot-core half, the Lenz lens, and the toroidal reactor in symmetrically coverage, to form the said flux suspension system;
   a first source of x-y excitation currents being applied to said x-y excitation winding distributions for generating a first hemispherical driving field fringing from the said annular sensing face;
   a software programable digital to analog x-y excitation current generator for generating at least a duality of first and second x-y current outputs, a selected first output of said duality, feeding the said first source of x-y excitation;
   the said software containing programable digital values for generation of at least the said selected first x-y output, and an auxiliary second x-y output.

2. The sensor according to claim 1, further defined as a variable-azimuthal concentric-hemispherical eddy current probe for generating at lest two concentric inner and outer driving hemispheres; and two asymmetric signals, comprising:
   an auxiliary toroid having inside and outside diameters, including first and second cylindrical ends, formed of a high permeability material, the outside diameter being tithtly fit with a auxiliary cylindrical Lenz lens formed of a high conductive material;
   said outer cylindrical Lenz lens further comprising, a longitudinal flange connected to a radial flange extending radially inward a distance equal to the radial thickness of the said outer toroid, the two flanges having a cross-section of several eddy current skin depths, the said second cylindrical end of the said auxiliary toroid disposed adjacent the said radial flange, the said first cylindrical end and the said longitudinal flange forming an auxiliary driving face;
   a high permeability toroid reactor core comprising two cylindrical ends and a winding window; the said reactor core being disposed concentrically with one cylindrical end, adjacent the said racial flange, to form an auxiliary eddy current driver;
   auxiliary x-y axes excitation winding distributions being wound through the said winding window as to encompass the auxiliary Lenz lens, the reactor core and the auxiliary toroid;
   auxiliary x-y axes excitation currents being applied to the said auxiliary x-y axes winding distributions from the said auxiliary second x-y output, for generating an azimuth selectable dipole diameterwise of the said auxiliary toroid, for inducing predetermined outer radii eddy currents in a conductive workpiece;
   the said auxiliary eddy current driver being concentrically disposed around the said polar coordinates sensor with the said annular sensing face of the said polar coordinates sensor and the said auxiliary driving face being coplanar to form the said variable-azimuthal concentric-hemispherical eddy current probe, for inducing an inner hemisphere and an outer hemisphere of eddy currents in the depth of a conductive workpiece, respective hemispheres having azimuthal independence, for generating the said asymmetric flux signal;

a digital signal processing means for extracting phase-amplitude elements contained in said asymmetric flux signal.

3. The eddy current probe according to claim 2, wherein the said inner and outer driving hemispheres are digitally programed to stepwise rotate by means of active/silent azimuthal increments independently including relative unidirectionally and bidirectionally.

4. The eddy current probe according to claim 2, where in the said inner and outer driving hemispheres rotate by sine-cosine excitation means, generating both relative uni-directional and bidirectional angular velocities.

5. A rod-type polar coordinates sensor having an improved flux suspension system for inducing an eddy current pattern in a conductive workpiece and for generating a flaw signal in response to an asymmetry in the said eddy current pattern; said sensor comprising:

a toroidal driving core formed of a high permeability material, taking the shape of a toroid having a rear radial plane, a driving radial plane, and a central bore;

a cylindrical driving flange formed of a high permeability material, disposed on the driving radial plane adjacent the outer diameter of the said bore forming a first winding window, the inside diameter of the driving flange, being equal to the inside diameter of the said bore;

a laminated Lenz lens formed of a stack of insulated thin high conductivity flat washers, having a central bore; the said Lenz lens being coaxially disposed around the said driving flange in contact with the said driving radial plane to form an annular focusing-sensing face;

a toroidal ballast core comprising a coaxial stack of at least two high permeability toroids, each having a central bore; the stacked bores forming a second winding window;

the said toroidal ballast core being disposed an adjustable displacement from the rear radial plane of the said toroidal driving core, with the said first and second winding windows coaxially aligned;

x-y excitation winding distributions shuttled through all the said winding windows, each turn encompassing the toroidal driving cor, the Lenz lens and the toroidal ballast core, forming the said improved flux suspension system;

x-y excitation currents being applied to the said x-y excitation windings for generating a fringing rotatable hemispherical flux pattern, diameterwise across the said focusing-sensing face;

the said x-y excitation currents being formed by predetermined software data stored in digital to analog x-y current generator for controlling the said hemispherical flux;

a pick-up core taking the shape of a high permeability rod, having sensing end and a flux return end;

the said pick-up core being disposed on the z-axis coaxially within the said first and second winding windows with the sensing end coplaner with the said focusing-sensing face and the flux return end in coaxial proximity with the longitudinal center of the toroidal ballast core, the said flux return end being the path for an asymmetric Lenz reflection in the said eddy current pattern;

a pick-up coil of many turns wound around the pick-up core, being disposed toward the sensing end, said pick-up coil for generating a signal in response to the said asymmetric Lenz reflect-on;

a saturable toroid core formed of a high permeability material, and toroidally wound with a saturating coil, defined as a toroid flux gate;

said flux gate being concentrically disposed around the said pick-up core near the longitudinal center;

a predetermined level of current flowing through the said saturating coil for modulating the said asymmetric Lenz reflection to extract additional phase-amplitude data.

6. A polar coordinates sensor comprising:

a high permeability toroidal core having x-y-z axes of permeability having a winding window disposed concentric with the z-axis; the said x-y axes of permeability lying in the equatorial plane of the toridal core;

the said toroidal core having x-y axes of magnetization coils wound through the said winding window and connected to x-y coordinates current sources controlled by a x-y coordinates pilot signal for inducing a hemispherical driving field fringing from the said equatorial plane;

a pick-up coil of many turns shunted by a series resonant variable capacitor;

the said pick-up coil being disposed coaxially on the z-axis within the said winding window for generating a signal in response to an asymmetry in the driving field flux;

said x-y coordinates pilot signal being formed by predetermined software within a digital computer means and interfaced with the said x-y coordinates current sources.

7. The invention according to claim 6, wherein the said predetermined software forms a x-y coordinates signal forming the said hemispherical driving field by means of a stepwise angular motion.

8. The invention according to claim 6, wherein the said x-y coordinates signal is the output of an electromechanical angular resolver having a x-y coordinates stator surrounding a rotor wound with an excitation winding excited by a pilot current modulated over a predetermined frequency range, including a direct current, the said output being connected to the said interface means.

9. The invention according to claim 1, further defined as a hidden metal edge mapper for use in aircraft splice-joint construction to detect a sub-layer edge by an asymmetric flux signal as the said sensor is scanned across the blind side.

10. The invention according to claim 9, wherein the said asymmetric flux signal comprises a deviation in phase angle, by means of tilting the z-axis of the said sensor toward/away from the direction of said scan, said deviation in phase angle for controlling automatic steering of a propelling and hidden edge marking means.

* * * * *